United States Patent
Hirose et al.

(10) Patent No.: US 11,540,711 B2
(45) Date of Patent: Jan. 3, 2023

(54) OPHTHALMOLOGIC APPARATUS AND METHOD FOR CONTROLLING THE SAME

(71) Applicant: TOPCON CORPORATION, Tokyo (JP)

(72) Inventors: Ryoichi Hirose, Itabashi-ku (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 462 days.

(21) Appl. No.: 16/731,229

(22) Filed: Dec. 31, 2019

(65) Prior Publication Data

US 2020/0214557 A1 Jul. 9, 2020

(30) Foreign Application Priority Data

Jan. 8, 2019 (JP) .............................. JP2019-001167

(51) Int. Cl.
*A61B 5/05* (2021.01)
*A61B 3/10* (2006.01)
*A61B 3/00* (2006.01)

(52) U.S. Cl.
CPC ............ *A61B 3/102* (2013.01); *A61B 3/0025* (2013.01)

(58) Field of Classification Search
CPC ......... A61B 3/102; A61B 3/0025; A61B 3/12; A61B 3/18; A61B 3/1025
(Continued)

(56) References Cited

U.S. PATENT DOCUMENTS

2015/0216408 A1   8/2015  Brown et al.
2018/0289260 A1   10/2018 Matsunobu et al.

FOREIGN PATENT DOCUMENTS

EP   3150109 A1   4/2017
JP   2015-534482 A   12/2015
(Continued)

OTHER PUBLICATIONS

Extended European Search Report dated Jun. 9, 2020 in European Patent Application No. 19219994.1, 7 pages.
(Continued)

*Primary Examiner* — Richard Tan
(74) *Attorney, Agent, or Firm* — Xsensus LLP

(57) ABSTRACT

An ophthalmologic apparatus, includes: a first concave mirror and a second concave mirror having a concave surface-shaped first reflective surface and a concave surface-shaped second reflective surface; an SLO optical system configured to project light from an SLO light source onto a subject's eye via the first concave mirror and the second concave mirror, and to detect returning light from the subject's eye; a first optical scanner configured to deflect the light from the SLO light source to guide the light to the first reflective surface; a second optical scanner configured to deflect light reflected by the first reflective surface to guide the light to the second reflective surface; an OCT optical system including a third optical scanner, and configured to split light from an OCT light source into measurement light and reference light, to project the measurement light deflected by the third optical scanner onto the subject's eye, and to detect interference light between returning light of the measurement light from the subject's eye and the reference light; an optical path coupling member disposed between the first optical scanner and the first concave mirror, and combining an optical path of the SLO optical system and an optical path of the OCT optical system; and a correction unit configured to correct detection result of the interference light detected by the OCT optical system or an image formed based on the detection result.

16 Claims, 6 Drawing Sheets

(58) Field of Classification Search
USPC .......................................................... 600/425
See application file for complete search history.

(56) References Cited

FOREIGN PATENT DOCUMENTS

| JP | 2017-064219 A | 4/2017 |
|---|---|---|
| JP | 2018-061622 A | 4/2018 |
| JP | 2018-167000 A | 11/2018 |
| WO | 2014/053824 A1 | 4/2014 |
| WO | 2018/069346 A1 | 4/2018 |

OTHER PUBLICATIONS

Office Action dated Jun. 21, 2022, in corresponding Japanese patent Application No. 2019-001167, 6 pages.

OPHTHALMOLOGIC APPARATUS AND METHOD FOR CONTROLLING THE SAME

CROSS-REFERENCE TO RELATED APPLICATION

This application is based upon and claims the benefit of priority from Japanese Patent Application No. 2019-001167, filed Jan. 8, 2019; the entire contents of which are incorporated herein by reference.

FIELD

The disclosure relates to an ophthalmologic apparatus and a method for controlling the same.

BACKGROUND

There is a demand for ophthalmologic apparatuses capable of easily observing and imaging fundus of a subject's eye with a wide field of view for screening or treating eye diseases. As such ophthalmologic apparatuses, scanning laser ophthalmoscopes (SLOs) are known. The SLO is an apparatus configured to form an image of the fundus by scanning the fundus with light to detect returning light of the light with a light receiving device.

Further, in recent years, attention has been drawn to optical coherence tomography (OCT) which is used to measure the morphology of an object to be measured or to image using light beam emitted from a laser light source or the like. Since OCT does not have invasiveness to human body as X-ray CT (Computed Tomography) does, development of application of OCT in medical field and biology field is particularly expected. Apparatuses using such OCT are applied to the diagnosis of various eye diseases, because of the ability to acquire high precision images.

For example, Japanese Unexamined Patent Application Publication No. 2018-61622 discloses an ophthalmologic apparatus for realizing the measurement function using SLO and the measurement function using OCT. In the ophthalmologic apparatus disclosed in Japanese Unexamined Patent Application Publication No. 2018-61622, the light on the combined optical path of the SLO optical system and the OCT optical system combined by the dichroic mirror is reflected by the slit mirror, the reflected light is deflected by the galvano mirror, is reflected by the ellipsoidal mirror, and is guided to the subject's eye. The galvano mirror is shared for scanning in the X direction of SLO and OCT.

SUMMARY

One aspect of some embodiments is an ophthalmologic apparatus, including: a first concave mirror having a concave surface-shaped first reflective surface; a second concave mirror having a concave surface-shaped second reflective surface; an SLO optical system configured to project light from an SLO light source onto a subject's eye via the first concave mirror and the second concave mirror, and to detect returning light from the subject's eye; a first optical scanner configured to deflect the light from the SLO light source to guide the light to the first reflective surface; a second optical scanner configured to deflect light reflected by the first reflective surface to guide the light to the second reflective surface; an OCT optical system including a third optical scanner, and configured to split light from an OCT light source into measurement light and reference light, to project the measurement light deflected by the third optical scanner onto the subject's eye, and to detect interference light between returning light of the measurement light from the subject's eye and the reference light; an optical path coupling member disposed between the first optical scanner and the first concave mirror, and combining an optical path of the SLO optical system and an optical path of the OCT optical system; and a correction unit configured to correct detection result of the interference light detected by the OCT optical system or an image formed based on the detection result.

Another aspect of some embodiments is a method of controlling an ophthalmologic apparatus including: a first concave mirror having a concave surface-shaped first reflective surface; a second concave mirror having a concave surface-shaped second reflective surface; an SLO optical system configured to project light from an SLO light source onto a subject's eye via the first concave mirror and the second concave mirror, and to detect returning light of the light from the subject's eye; a first optical scanner configured to deflect the light from the SLO light source to guide the light to the first reflective surface; a second optical scanner configured to deflect light reflected by the first reflective surface to guide the light to the second reflective surface; an OCT optical system including a third optical scanner, and configured to split light from an OCT light source into measurement light and reference light, to project the measurement light deflected by the third optical scanner onto a subject's eye, and to detect interference light between returning light of the measurement light from the subject's eye and the reference light; and an optical path coupling member disposed between the first optical scanner and the first concave mirror, and combining an optical path of the SLO optical system and an optical path of the OCT optical system, the method including: an acquisition step of acquiring detection result of the interference light by performing optical coherence tomography on the subject's eye using the OCT optical system; and a correction step of correcting the detection result of the interference light acquired in the acquisition step or an image formed based on the detection result.

DETAILED DESCRIPTION

Figure 1:
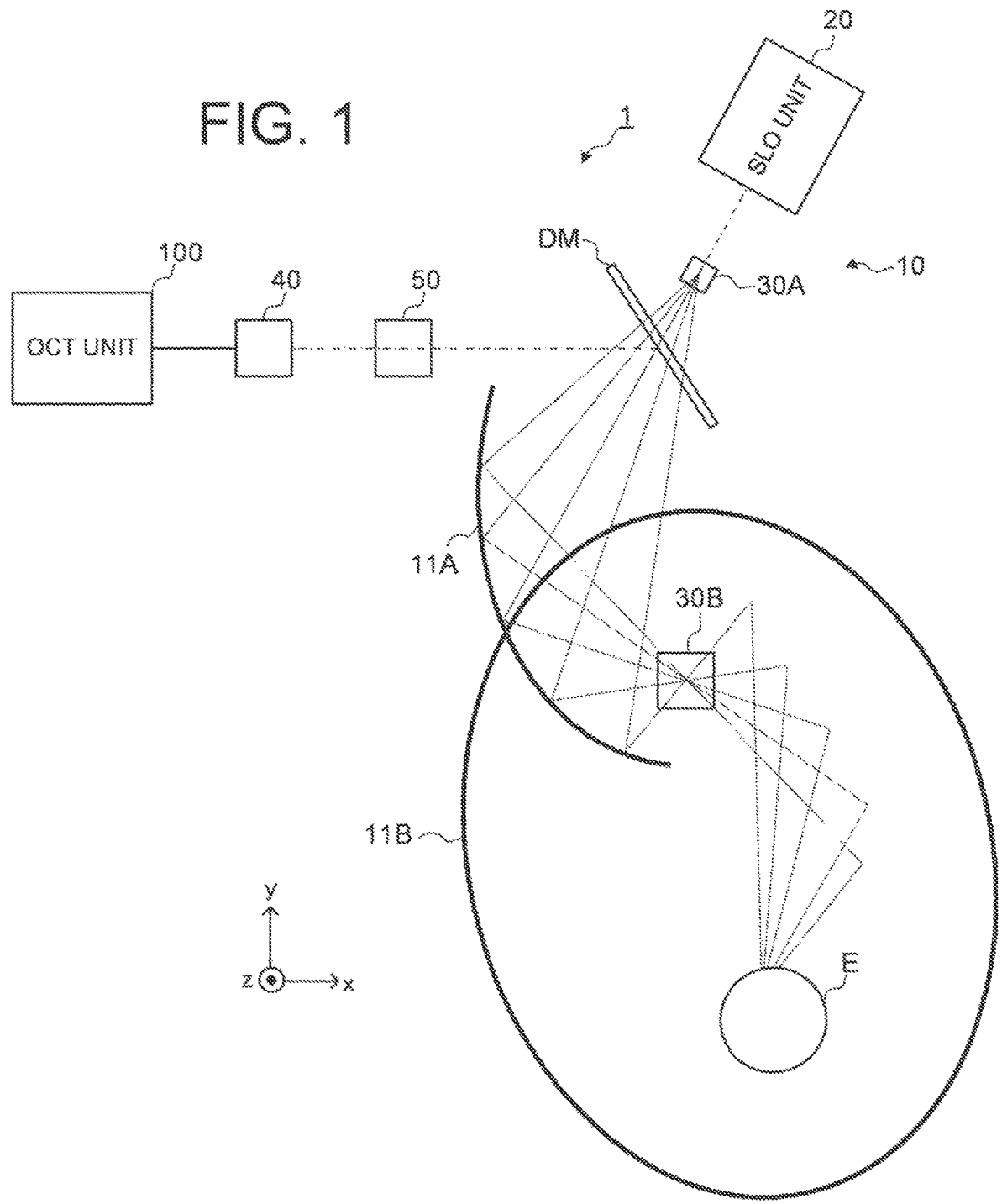
FIG. 1 is a schematic diagram illustrating an example of the configuration of an ophthalmologic apparatus according to embodiments.

For optical systems including an ellipsoidal mirror for measuring a subject's eye at a wide angle, high processing accuracy is required. High processing accuracy leads to an increase in processing cost. Thereby, it is necessary to perform measurement within a predetermined allowable error range in consideration of a trade-off between measurement accuracy and processing cost.

Further, SLO and OCT have different scan speeds. Therefore, when the optical scanner is simply shared between SLO and OCT, an expensive optical scanner needs to be used or the optical scanner control becomes complicated. On the other hand, when an optical scanner for SLO and an optical scanner for OCT are provided, at least one optical scanner is disposed at a position out of the focal position of the ellipsoidal mirror. Thereby, the optical path length changes depending on the deflection angle of the light, resulting in a decrease in measurement accuracy.

The above situation is not limited to ophthalmologic apparatuses using an ellipsoidal mirror. The same applies to ophthalmologic apparatuses using a concave mirror having a concave-shaped reflective surface.

According to some embodiments of the present invention, an ophthalmologic apparatus capable of performing OCT measurement using a concave mirror with a wider angle at low cost, and a method of controlling the ophthalmologic apparatus can be provided.

Referring now to the drawings, exemplary embodiments of an ophthalmologic apparatus and a method of controlling the ophthalmologic apparatus according to the present invention are described below. Any of the contents of the documents cited in the present specification and arbitrary known techniques may be applied to the embodiments below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The ophthalmologic apparatus according to embodiments includes an SLO optical system and an OCT optical system. The ophthalmologic apparatus can perform SLO measurement and OCT measurement. The SLO optical system is an optical system configured to project light from an SLO light source onto a subject's eye, and to detect returning light from the subject's eye. The OCT optical system is an optical system configured to split light from an OCT light source into measurement light and reference light, to project the measurement light onto a subject's eye, to generate interference light between returning light from the subject's eye and the reference light, and to detect the generated interference light. The SLO measurement is measurement (imaging) using the SLO optical system. The OCT measurement is measurement (imaging) using the OCT optical system.

The ophthalmologic apparatus includes a first concave mirror and a second concave mirror. The ophthalmologic apparatus is configured to irradiate the light from the SLO light source or the measurement light (light from the OCT light source) to a wide measurement range on the subject's eye via the first concave mirror and the second concave mirror. Specifically, the ophthalmologic apparatus includes a first optical scanner and a second optical scanner which are arranged at positions suitable for SLO measurement and which are capable of one-dimensionally deflecting light in directions crossing each other. The ophthalmologic apparatus can scan a fundus of a subject's eye at a wide angle with the light from the SLO light source. The first optical scanner and the second optical scanner are disposed at positions optically conjugate with a pupil of the subject's eye (pupil conjugate positions) or near the positions.

Further, the ophthalmologic apparatus includes a third optical scanner and an optical path combining member. The optical path coupling member couples an optical path of the OCT optical system with an optical path of the SLO optical system. The ophthalmologic apparatus can scan the subject's eye with the measurement light deflected by the third optical scanner via the first concave mirror and the second concave mirror. The third optical scanner deflects the measurement light in a one-dimensionally or two-dimensional manner. When the third optical scanner deflects the measurement light one-dimensionally, the third optical scanner can be arranged at the pupil conjugate position or near the position. When the third optical scanner deflects the measurement light two-dimensionally, one of two optical scanners included in the third optical scanner can be arranged at the pupil conjugate position or near the position. The ophthalmologic apparatus corrects data of the subject's eye (for example, tomographic image) acquired using the OCT optical system, using correction data stored in advance.

With such a configuration, a decrease in measurement accuracy limited due to the tolerance of the optical system can be compensated. Thereby, a more accurate measurement result can be obtained. That is, a more accurate measurement result can be obtained regardless of the tolerance of the optical system. Further, when the third optical scanner deflects the measurement light two-dimensionally, unnatural distortion in the depth direction depending on the deflection angle of the optical scanner (third optical scanner) caused by the arrangement position of the third optical scanner can be corrected. Thereby, a tomographic image similar to the case where a conventional lens optical system is used can be acquired. Moreover, it is not necessary to relay the conjugate position of the pupil of the subject's eye in order to arrange the third optical scanner. Thereby, the optical system of apparatus can be downsized.

Hereinafter, in the embodiments, the case of using the swept source type OCT method in the measurement or the imaging (photographing) using OCT will be described. However, the configuration according to the embodiments can also be applied to an ophthalmologic apparatus using other type of OCT (for example, spectral domain type OCT).

Hereinafter, the case in which the optical scanner includes a galvano scanner will be described. However, the following embodiments can also be applied when the optical scanner includes a deflection element other than the galvano scanner (for example, a resonant mirror, a polygon mirror, etc.).

In this specification, images acquired using SLO may be collectively referred to as "SLO images" and images acquired using OCT may be collectively referred to as "OCT images". Also, the measurement operation for forming SLO images may be referred to as SLO measurement and the measurement operation for forming OCT images may be referred to as OCT measurement.

The ophthalmologic apparatus according to some embodiments further includes any one or more of an ophthalmologic imaging apparatus, an ophthalmologic measuring apparatus, and an ophthalmologic therapy apparatus. The ophthalmologic imaging apparatus included in the ophthalmologic apparatus according to some embodiments includes, for example, any one or more of a fundus camera, a slit lamp ophthalmoscope, a surgical microscope, and the like. Further, the ophthalmologic measuring apparatus included in the ophthalmologic apparatus according to some embodiments includes any one or more of an eye refractivity examination apparatus, a tonometer, a specular microscope, a wave-front analyzer, a perimeter, a microperimeter, and the like, for example. Further, the ophthalmologic therapy apparatus included in the ophthalmologic apparatus according to some embodiments includes any one or more of a laser therapy apparatus, a surgical apparatus, a surgical microscope, and the like, for example.

Hereinafter, an ophthalmologic apparatus capable of performing OCT measurement on a fundus of the subject's eye will be described as an example. However, the ophthalmologic apparatus according to the embodiments may be capable of performing OCT measurement on an anterior segment of the subject's eye. In some embodiments, a measurement site of the OCT measurement and/or a range of the OCT measurement are changed by moving a lens for changing focal position of the measurement light. In some embodiments, the ophthalmologic apparatus has a configuration capable of performing OCT measurement on the fundus, OCT measurement on the anterior segment, and OCT measurement on the whole eyeball including the fundus and anterior segment, by adding one or more attachments (objective lens, front lens, etc.). In some embodiments, in the ophthalmologic apparatus for measuring fundus, OCT measurement is performed on the anterior segment, by making the measurement light incident on the subject's eye, the measurement light having been converted into a parallel light flux by arranging a front lens between a collimator lens unit (described later) or an optical scanner and the subject's eye.

<Configuration>

FIG. 1 illustrates an example of the configuration of the ophthalmologic apparatus according to the embodiments.

The ophthalmologic apparatus 1 according to the embodiments includes an optical system 10, an SLO unit 20, and an OCT unit 100. The optical system 10 includes a first ellipsoidal mirror 11A, a second ellipsoidal mirror 11B, optical scanners 30A and 30B, a collimator lens unit 40, an optical scanner 50, and a dichroic mirror DM. The optical scanner 30A is an example of the first optical scanner. The optical scanner 30B is an example of the second optical scanner. The optical scanner 50 is an example of the third optical scanner. In some embodiments, the SLO unit 20 includes the optical scanners 30A and 30B. In some embodiments, the OCT unit 100 includes the collimator lens unit 40 and the optical scanner 50.

A reflective surface (first reflective surface) of the first ellipsoidal mirror 11A is an elliptical surface. The first ellipsoidal mirror 11A is an example of the concave mirror. In some embodiments, the optical system 10 includes a concave mirror whose reflective surface is formed in a concave shape, instead of the first ellipsoidal mirror 11A. In some embodiments, the reflective surface of the concave mirror is formed to be a free-form surface.

A reflective surface (second reflective surface) of the second ellipsoidal mirror 11B is an elliptical surface. The second ellipsoidal mirror 11B is an example of the concave mirror. In some embodiments, the optical system 10 includes a concave mirror whose reflective surface is formed in a concave shape, instead of the second ellipsoidal mirror 11B. In some embodiments, the reflective surface of the concave mirror is formed to be a free-form surface.

The first ellipsoidal mirror 11A has two optically conjugate focal points (first focal point, second focal point). The optical scanner 30A (deflected surface of the optical scanner 30A) is disposed at the first focal point of the first ellipsoidal mirror 11A, near the first focal point, a position optically conjugate with the first focal point (conjugate position of the first focal point), or near the position optically conjugate with the first focal point. The optical scanner 30B (deflected surface of the optical scanner 30B) is disposed at the second focal point of the first ellipsoidal mirror 11A, near the second focal point, a position optically conjugate with the second focal point (conjugate position of the second focal point), or near the position optically conjugate with the second focal point.

The second ellipsoidal mirror 11B has two optically conjugate focal points (third focal point, fourth focal point). The third focal point of the second ellipsoidal mirror 11B is arranged so as to coincide with the second focal point of the first ellipsoidal mirror 11A. The optical scanner 30B (deflected surface of the optical scanner 30B) is disposed at the third focal point of the second ellipsoidal mirror 11B, near the third focal point, a position optically conjugate with the third focal point (conjugate position of the third focal point), or near the position optically conjugate with the third focal point. The subject's eye position, where the subject's eye E (pupil) is arranged, is disposed at the fourth focal point of the second ellipsoidal mirror 11B, near the fourth focal point, a position optically conjugate with the fourth focal point (conjugate position of the sixth focal point), or near the position optically conjugate with the fourth focal point.

Each of the optical scanners 30A and 30B is a uniaxial optical scanner. The optical scanner 30A deflects the light from the SLO light source in a predetermined deflection direction. The optical scanner 30B deflects the light from the SLO light source, which is deflected by the optical scanner 30A, in a direction orthogonal to (intersecting) the above deflection direction. The optical scanners 30A and 30B are respectively disposed at positions optically conjugate with the pupil of the subject's eye E (pupil conjugate position) or near the positions. That is, by two-dimensionally deflecting the light from the SLO light source using the optical scanners 30A and 30B, a predetermined site on the fundus Ef of the subject's eye is scanned.

Each of the optical scanners 30A and 30B includes a mirror whose inclination can be changed. In each of the optical scanners 30A and 30B, the inclination of the reflective surface is controlled under the control of a controller 200 (main controller 201) described later. Each of the optical scanners 30A and 30B deflects light one-dimensionally in the SLO measurement under the control of the controller 200 (main controller 201) described later. The optical scanner 30A is used for scanning in a horizontal direction (x direction) of the fundus plane, for example. The optical scanner 30B is used for scanning in a vertical direction (y direction), which is orthogonal to the horizontal direction, of the fundus plane, for example. Either one of the optical scanners 30A and 30B may be a low-speed scanner such as a galvano mirror, and the other may be a high-speed scanner such as a resonant mirror, a polygon mirror, or a microelectromechanical systems (MEMS) mirror. For example, the optical scanner 30A is a high-speed scanner, and the optical scanner 30B is a low-speed scanner. Examples of scan mode with the light from the SLO light source performed by the optical scanners 30A and 30B include horizontal scan, vertical scan, cross scan, radial scan, circle scan, concentric scan, helical (spiral) scan, and the like.

The optical scanner 30A deflects the light from the SLO light source to guide the deflected light to the first reflective surface of the first ellipsoidal mirror 11A. The optical scanner 30B deflects the light reflected by (on) the first reflective surface to guide the deflected light to the second reflective surface of the second ellipsoidal mirror 11B. The light reflected by the second reflective surface is guided to the subject's eye position.

The dichroic mirror DM is arranged between the optical scanner 30A and the first ellipsoidal mirror 11A (first reflective surface). The light from the SLO unit 20 is transmitted through the dichroic mirror DM and is guided to the subject's eye E. Returning light from the subject's eye E is transmitted through the dichroic mirror DM and is guided to the SLO unit 20. The measurement light from the OCT unit 100 is reflected toward the subject's eye E by the dichroic mirror DM. Returning light of the measurement light from the subject's eye E is reflected toward the OCT unit 100 by the dichroic mirror DM.

The optical scanner 50 is disposed at the pupil conjugate position or near the pupil conjugate position. The optical scanner 50 deflects measurement light (measurement light traveling along the optical path for OCT) emitted from the collimator lens unit 40 in a predetermined deflection angle range. The optical scanner 50 can deflect the measurement light in a one-dimensionally or two-dimensional manner.

When the optical scanner 50 deflects the measurement light one-dimensionally, a predetermined site on the fundus Ef of the subject's eye is scanned two-dimensionally by two-dimensionally deflecting the measurement light using the optical scanners 50 and 30B.

Further, when the optical scanner 50 deflects the measurement light two-dimensionally, a predetermined site on the fundus Ef of the subject's eye is scanned two-dimensionally. In this case, the optical scanner 50 includes a first galvano scanner and a second galvano scanner. The first galvano scanner deflects the measurement light so as to scan a photographing (imaging) site (fundus Ef or the anterior segment) in the horizontal direction orthogonal to (intersecting) the optical path (optical axis) of the measurement light. The second galvano scanner deflects the measurement light deflected by the first galvano scanner so as to scan the photographing site in the vertical direction orthogonal to (intersecting) the optical path (optical axis) of the measurement light. Examples of scan mode with the measurement light performed by the optical scanner 50 include horizontal scan, vertical scan, cross scan, radial scan, circle scan, concentric scan, helical (spiral) scan, and the like.

The optical scanner 50 can deflect the measurement light one-dimensionally or two-dimensionally by at least one of the first galvano scanner and the second galvano scanner in the OCT measurement, under the control of the controller 200 (main controller 201) described later. That is, the subject's eye can be scanned one-dimensionally or two-dimensionally by controlling the optical scanner 50 to scan alone. Further, the optical scanners 50 and 30B can scan the subject's eye E two-dimensionally under the control of the controller 200 described later.

The collimator lens unit 40 includes a collimator lens. The collimator lens is disposed on an optical axis of an interference optical system included in the OCT unit 100. The collimator lens converts a light flux of the measurement light emitted from the end of an optical fiber into a parallel light flux. The optical fiber is connected to the OCT unit 100 and guides the measurement light to the end. The end of this optical fiber is, for example, located at a position optically substantially conjugate with the fundus Ef (retina) of the subject's eye E (fundus conjugate position) or near the position.

In addition to the configuration illustrated in FIG. 1, the optical system 10 may be provided with an optical system (observation optical system, imaging optical system, etc.) for photographing the subject's eye E (fundus Ef or the anterior segment) from the front, and/or an alignment optical system.

Further, the optical system 10 may have a configuration for providing a function associated with the inspection. For example, the optical system 10 may include a fixation optical system for projecting a visual target (fixation target) for fixating the subject's eye E onto the fundus Ef of the subject's eye E. Further, the optical system 10 may also be provided with a configuration for focusing of the interference optical system included in the OCT unit 100 and the like. The optical system 10 may be further provided with a light source (anterior segment illumination light source) for illuminating the anterior segment of the subject's eye E.

The SLO unit 20 is provided with an optical system for performing SLO measurement (SLO optical system). The OCT unit 100 is provided with an optical system for performing OCT (interference optical system, OCT optical system).

In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic apparatus 1. In some embodiments, the lens unit is configured to be manually inserted and removed between the subject's eye E and an objective lens (not shown). In some embodiments, the lens unit is configured to be automatically inserted and removed between the subject's eye E and the objective lens, under the control of the controller 200 described later.

[SLO Unit 20]

Figure 2:
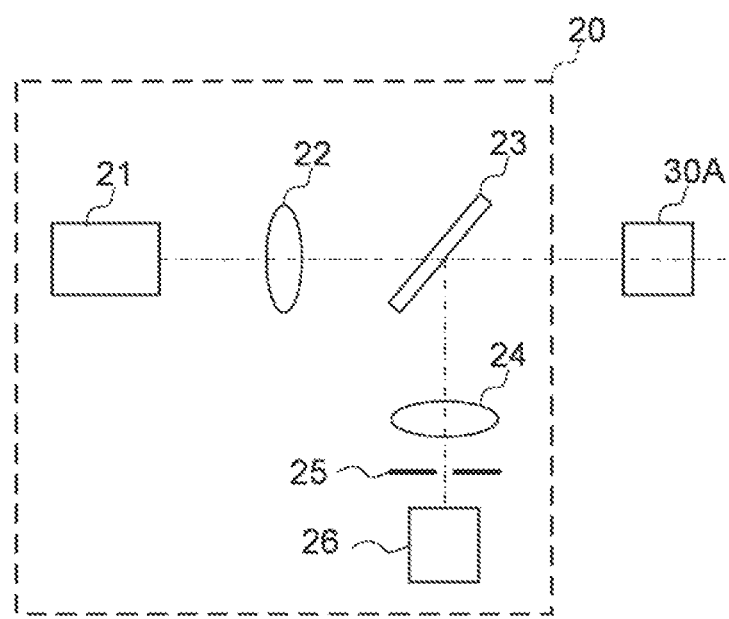
FIG. 2 is a schematic diagram illustrating an example of the configuration of an ophthalmologic apparatus according to embodiments.

An example of the configuration of the SLO unit 20 of FIG. 1 is shown in FIG. 2. In FIG. 2, like reference numerals designate like parts as in FIG. 1. The same description may not be repeated.

The SLO unit 20 includes an SLO light source 21, a collimator lens 22, a beam splitter 23, a condenser lens 24, a confocal diaphragm 25, and a detector 26. The beam splitter 23 is an optical path coupling member configured to couple an optical path of light from the SLO light source 21 projected onto the subject's eye E (SLO light) with an optical path of returning light of the SLO light.

The SLO light source 21 emits light having a center wavelength of 840 nm, for example. Examples of the SLO light source 21 include a laser diode (LD), a super-luminescent diode (SLD), a laser-driven light source (LDLS), and the like. The SLO light source 21 is arranged at the fundus conjugate position or near the fundus conjugate position.

Light emitted from the SLO light source 21 is collimated into a parallel light flux by the collimator lens 22. The light collimated into the parallel light flux is transmitted through the beam splitter 23. The light transmitted through the beam splitter 23 is deflected in a predetermined deflection direction (for example, x direction) by the optical scanner 30A, is transmitted through the dichroic mirror DM, and is guided to the first reflective surface of the first ellipsoidal mirror 11A. Light reflected by the first reflective surface is deflected in a predetermined deflection direction (for example, y direction) by the optical scanner 30B, and is guided to the second reflective surface of the second ellipsoidal mirror 11B. Light reflected by the second reflective surface enters the eye through the pupil of the subject's eye E at the subject's eye position.

The light from the SLO light source 21 that has entered the eye of the subject's eye E is reflected on the fundus Ef. Reflected light, which is returning light of the light incident on the eye, travels in the opposite direction on the same path as the outward and is reflected toward the detector 26 by the beam splitter 23. The condenser lens 24 and the confocal diaphragm 25 are arranged between the beam splitter 23 and the detector 26. The condenser lens 24 condenses the light reflected by the beam splitter 23. The light condensed by the condenser lens 24 passes through an opening formed in the confocal diaphragm 25, and enters a detection surface of the detector 26. The opening formed in the confocal diaphragm 25 is arranged at the fundus conjugate position or near the fundus conjugate position. The detector 26 is made of, for example, an avalanche photodiode (APD) or a photomultiplier tube (PMT).

[OCT Unit 100]

Figure 3:
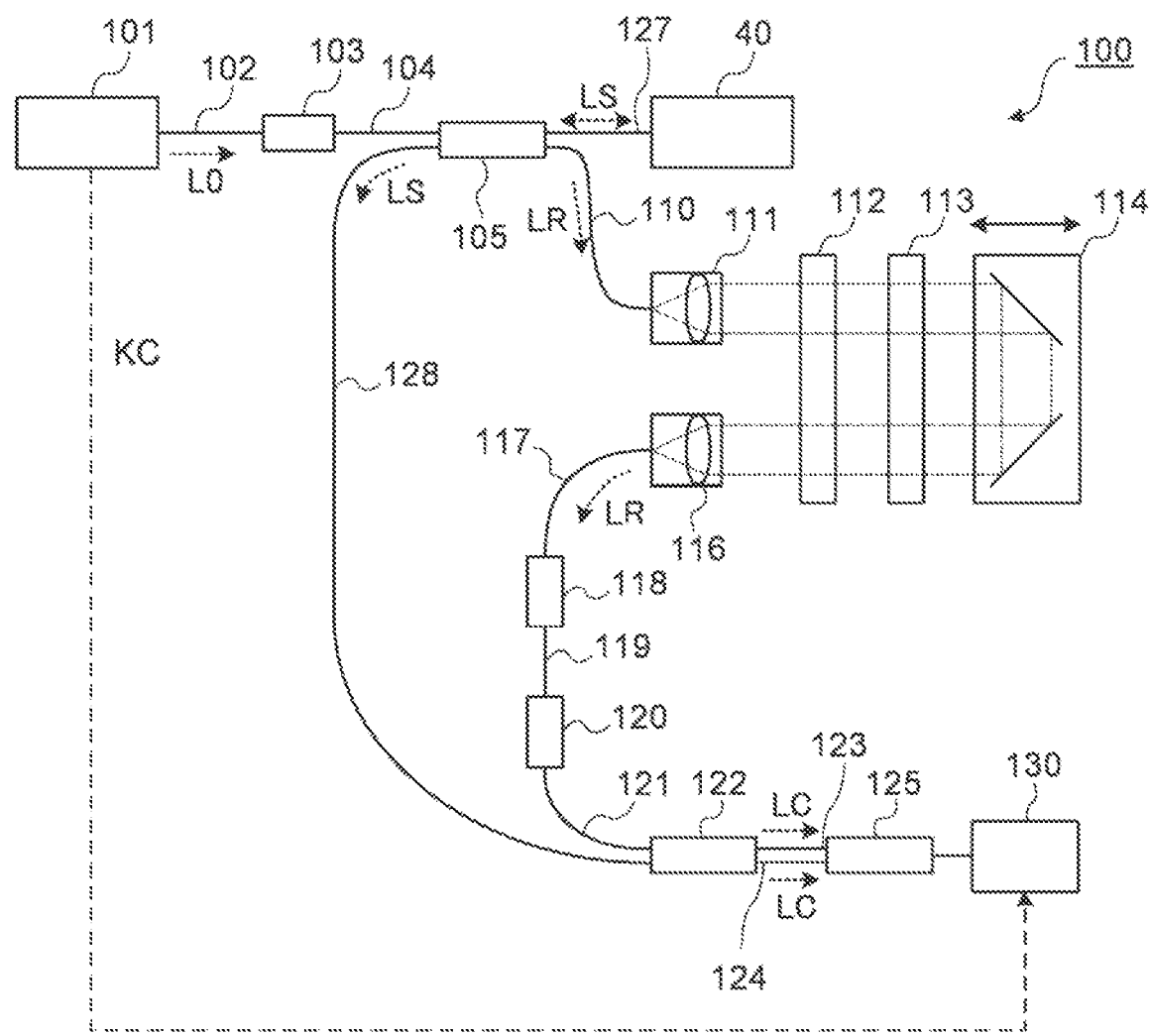
FIG. 3 is a schematic block diagram illustrating an example of the configuration of the ophthalmologic apparatus according to the embodiments.

An example of the configuration of the OCT unit 100 of FIG. 1 is shown in FIG. 3. In FIG. 3, like reference numerals designate like parts as in FIG. 1, and the redundant explanation may be omitted as appropriate.

The OCT unit 100 is provided with an optical system for acquiring OCT images of the subject's eye E. The optical system includes an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result (detection signal) of the interference light obtained by the interference optical system is a signal indicating a spectrum of the interference light, and is sent to the image forming unit 210, the data processor 220, and the like which are described later.

Like swept source type ophthalmologic apparatuses commonly used, the OCT light source 101 includes a wavelength sweeping type (i.e., a wavelength scanning type) light source capable of sweeping (scanning) the wavelengths of emitted light. A laser light source including a resonator and emitting light having a center wavelength of 1050 nm, for example, is used as the wavelength sweeping type light source. The OCT light source 101 temporally changes the output wavelength in the near infrared wavelength band which cannot be visually recognized by the human eye.

Light L0 output from the OCT light source 101 is guided to the polarization controller 103 through the optical fiber 102, and the polarization state of the light L0 is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light beam by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS.

The optical path length changing unit 114 is movable in directions indicated by the arrow in FIG. 3, thereby changing the length of the optical path of the reference light LR. Through such movement, the length of the optical path of the reference light LR is changed. The change in the optical path length is used for the correction of the optical path length according to the axial length of the subject's eye E, for the adjustment of the interference state, or the like. The optical path length changing unit 114 includes, for example, a corner cube and a movement mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The reference light LR that has traveled through the optical path length changing unit 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through the optical fiber 127, and is made into the parallel light beam by the collimator lens unit 40. The measurement light LS, which has been made into a parallel light beam, is one-dimensionally or two-dimensionally deflected by the optical scanner 50, is reflected by the dichroic mirror DM, and is guided to the first reflective surface of the first ellipsoidal mirror 11A. The measurement light LS reflected by the first reflective surface is deflected by the optical scanner 30B with the deflected surface fixed, and is guided to the second reflective surface of the second ellipsoidal mirror 11B. In some embodiments, the orientation of the deflected surface of the optical scanner 30B is controlled depending on the measurement site in the subject's eye E (fundus Ef). The measurement light LS reflected by the second reflective surface enters the eye through the pupil of the subject's eye E at the subject's eye position. The measurement light LS is scattered (and reflected) at various depth positions of the subject's eye E. The returning light of the measurement light LS including such backscattered light advances through the same path as the outward path in the opposite direction and is led to the fiber coupler 105, and then reaches the fiber coupler 122 through the optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. A clock KC is supplied from the OCT light source 101 to the DAQ 130. The clock KC is generated in the OCT light source 101 in synchronization with the output timing of each wavelength sweeping (scanning) within a predetermined wavelength range performed by the wavelength sweeping type light source. For example, the OCT light source 101 optically delays one of the two pieces of branched light obtained by branching the light L0 of each output wavelength, and then generates the clock KC based on the result of the detection of the combined light of the two pieces of branched light. The DAQ 130 performs sampling of the detection result obtained by the detector 125 based on the clock KC. The DAQ 130 sends the result of the sampling of the detection result obtained by the detector 125 to the image forming unit 210, the data processor 220, and the like which are described later. The image forming unit 210 and the data processor 220 etc. which are described later apply Fourier transform and the like to the spectral distribution based on the detection result obtained by the detector 125, for example, with respect to a series of wavelength scans (for each A-line) to form the reflection intensity profile in each A-line. In addition, the image forming unit 210 forms image data by applying imaging processing to the reflection intensity profiles of the respective A lines.

Figure 4:
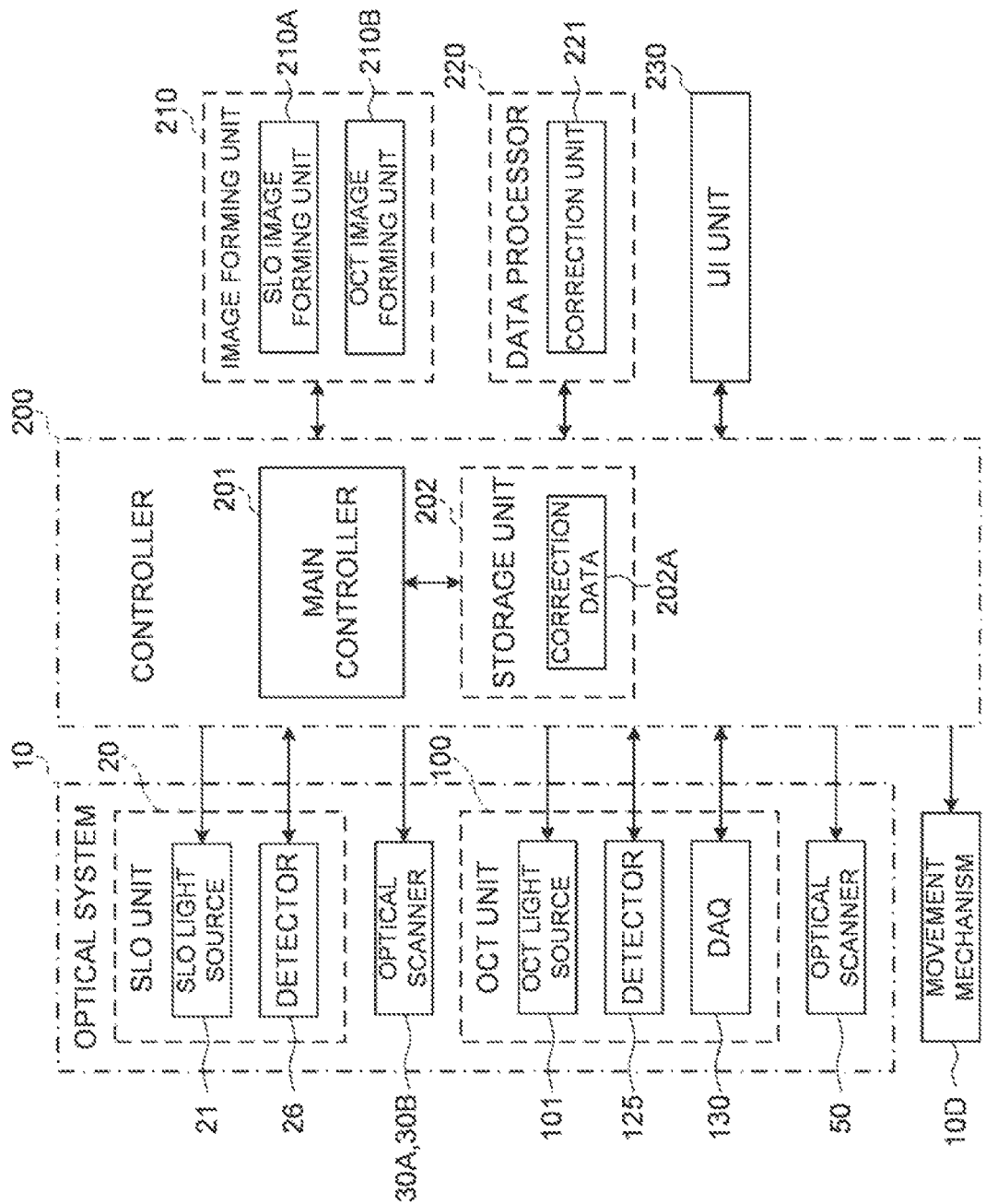
FIG. 4 is a schematic diagram illustrating an example of the configuration of an ophthalmologic apparatus according to embodiments.

FIG. 4 illustrate an example of the configuration of the processing system of the ophthalmologic apparatus 1 according to the embodiments. In FIG. 4, parts similar to those in FIGS. 1 to 3 are denoted by the same reference symbols, and description thereof is omitted as appropriate.

The processing system of the ophthalmologic apparatus 1 is configured with the controller 200 as a center. The controller 200 controls each part of the ophthalmologic apparatus 1. The controller 200 includes the main controller 201 and a storage unit 202. The functions of the main controller 201 are implemented by a processor, for example. The storage unit 202 stores, in advance, a computer program for controlling the ophthalmologic apparatus 1. The computer program includes, for example, various light source control programs, optical scanner control program, various detector control programs, image forming program, data processing program, program for user interface, and the like. The main controller 201 (processor) operates according to the computer programs, and thereby the controller 200 performs the control process.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

(Main Controller 201)

The main controller 201 controls each of the optical system 10, the image forming unit 210, the data processor 220, and the user interface (UI) unit 230.

Examples of the control of the optical system 10 include control of the SLO optical system, control of the OCT optical system, and the like.

Examples of the control of the SLO optical system include control of the SLO unit 20, control of the optical scanners 30A and 30B, and the like. Examples of the control of the optical scanners 30A and 30B include control of the scan position, the scan range, and the scan speed using the optical scanner 30A, control of the scan position, the scan region, and the scan speed using the optical scanner 30B, and the like. Examples of the control of the SLO unit 20 include control of the SLO light source 21, control of the detector 26, and the like. Examples of the control of the SLO light source 21 include turning on and off the light source, adjustment of the amount of light, adjustment of an aperture, and the like. Examples of the control of the detector 26 include adjustment of exposure of a detecting element, adjustment of gain of a detecting element, adjustment of detecting rate of a detecting element, and the like.

Examples of the control of the OCT optical system include control of the OCT unit 100, control of the optical scanner 50, and the like. Examples of the control of the OCT unit 100 include control of the OCT light source 101, control of the detector 125, control of the DAQ 130, and the like. Examples of the control of the OCT light source 101 include turning on and off the light source, adjustment of the amount of light, adjustment of an aperture, and the like. Examples of the control of the detector 125 include adjustment of exposure of a detecting element, adjustment of gain of a detecting element, adjustment of detecting rate of a detecting element, and the like.

Examples of the control of the optical scanner 50 include control of the scan position, the scan range, and the scan speed, the scan direction, and the like using the optical scanner 50. When the optical scanner 50 includes the first galvano scanner and the second galvano scanner as described above, examples of the control of the optical scanner 50 include control of the scan position, the scan range, and the scan speed using the aforementioned first galvano scanner, control of the scan position, the scan range, and the scan speed using the aforementioned second galvano scanner, and the like.

As a first control example, the main controller 201 (controller 200) performs control so that the optical scanner 30B is shared for SLO measurement and OCT measurement. Specifically, the main controller 201 controls, in the SLO measurement mode, the optical scanner 30A so as to one-dimensionally deflect the light from the SLO light source 21 in the x direction (first direction), and controls the optical scanner 30B so as to one-dimensionally deflect the light deflected by the optical scanner 30A in the y direction (second direction). The main controller 201 controls, in the OCT measurement mode, the optical scanner 50 so as to one-dimensionally deflect the measurement light LS in the x direction (third direction), and controls the optical scanner 30B so as to one-dimensionally deflect the measurement light LS deflected by the optical scanner 50 in the y direction (fourth direction).

As a second control example, the main controller 201 (controller 200) controls to stop the deflection operation of the optical scanner 30B during OCT measurement. Specifically, the main controller 201 controls, in the SLO measurement mode, the optical scanner 30A so as to one-dimensionally deflect the light from the SLO light source 21 in the x direction (first direction), and controls the optical scanner 30B so as to one-dimensionally deflect the light deflected by the optical scanner 30A in the y direction (second direction). The main controller 201 sets, in the OCT measurement mode, the orientation of the deflected surface of the optical scanner 30B so that the measurement light LS is irradiated in a range corresponding to the measurement site, and controls the optical scanner 50 to deflect the measurement light LS two-dimensionally with the deflection operation of the optical scanner 30B stopped.

Further, as the control of the OCT unit 100, the main controller 201 can control the operation of the optical path length changing unit 114; the operations of the attenuator 120; the operation of the polarization controllers 103 and 118; and the like.

Further, the main controller 201 can control the fixation optical system (not shown) to present the fixation target to the subject's eye E so as to guide fixation to the fixation position set manually or automatically.

Further, the main controller 201 can control a focusing lens (not shown) to move the focusing lens in the optical axis direction of the interference optical system to change the focus point of the measurement light. For example, the focus position of the measurement light LS can be arranged at the fundus Ef or near the fundus Ef by moving the focusing lens to a first lens position. For example, by moving the focusing lens to a second lens position, the focus position of the measurement light can be arranged at a far point position and the measurement light LS can be made into a parallel light beam. The focus position of the measurement light LS corresponds to the depth position (z position) of the beam waist of the measurement light LS.

Further, the main controller 201 can control the movement mechanism 10D. The movement mechanism 10D three-dimensionally moves at least a part of the optical system 10 (for example, interference optical system), for example. In a typical example, the movement mechanism 10D includes a mechanism for moving at least the optical system 10 in the x direction (left-right direction, horizontal direction), a mechanism for moving it in the y direction (up-down direction, vertical direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 201.

The control for the movement mechanism 10D is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 10D is configured to be controlled to change the optical path length of the reference light (that is, the difference of the optical path length between the optical path of the measurement light and the optical path of the reference light).

In the case of manual alignment, a user operates the user interface (UI) unit 230 described later to relatively move the optical system and subject's eye E so as to cancel the displacement of the subject's eye E with respect to the optical system. For example, the main controller 201 controls the movement mechanism 10D to relatively move the optical system and the subject's eye E by outputting a control signal corresponding to the operation content with respect to the user interface unit 230 to the movement mechanism 10D.

In the case of automatic alignment, the main controller 201 controls the movement mechanism 10D to relatively move the optical system and the subject's eye E so as to cancel the displacement of the subject's eye E with respect to the optical system. For example, the movement mechanism 10D is controlled so as to cancel a displacement between (a reference position of) the image of the subject's eye E acquired using imaging optical system (not shown) and a reference position of the optical system. In some embodiments, the main controller 201 controls the movement mechanism 10D to relatively move the optical system and the subject's eye E by outputting a control signal to the movement mechanism 10D so that the optical axis of the optical system substantially coincides with the axis of the subject's eye E and the distance of the optical system with respect to the subject's eye E is a predetermined working distance. Here, the working distance is a preset value which is called a working distance of the objective lens (not shown), and it means the distance between the subject's eye E and the optical system when measuring (imaging) using the optical system.

The main controller 201 can control each of the above units (parts) according to the designated operation mode. The main controller 201 controls the SLO unit 20 etc. to control the SLO measurement, in the SLO measurement mode. The main controller 201 controls the OCT unit 100 etc. to control the OCT measurement, in the OCT measurement mode.

For example, the main controller 201 is capable of performing a plurality of preliminary operations prior to the OCT measurement. The preliminary operations may include alignment, focus adjustment, optical path length difference adjustment, polarization adjustment, and the like. The plurality of preliminary operations is performed in a predetermined order. In some embodiments, the plurality of preliminary operations is performed in an order described above.

It should be noted that the types and the orders of the preliminary operations are not so limited, and they may be optional. For example, the preliminary operations may further include small-pupil judgment. The small-pupil judgment is a preliminary operation to judge whether the pupil of the subject's eye E is small or not (whether the subject's eye E is microcoria or not). The small-pupil judgment may be performed between the rough focus adjustment and the optical path length difference adjustment. In some embodiments, the small-pupil judgment includes, for example, a series of processes as follows: acquiring a front image (anterior segment image) of the subject's eye E; specifying an image region corresponding to the pupil; calculating the size (e.g., diameter, circumference length) of the pupil region; judging whether the pupil of the subject's eye E is small or not based on the calculated size (threshold processing); and controlling a diaphragm (not shown) when judged that the pupil of the subject's eye E is small. In some embodiments, the calculation of the size of the pupil region includes processing of circularly or elliptically approximating the pupil region.

The focus adjustment is performed on the basis of interference sensitivity of OCT measurement, for example. For example, the focus adjustment can be performed by: monitoring interference intensity (interference sensitivity) of interference signal acquired by performing OCT measurement of the subject's eye E; searching the position of the focusing lens so as to maximize the interference intensity; and moving the focusing lens to the searched position.

To perform the optical path length difference adjustment, the optical system is controlled so that a predetermined position on the subject's eye E is a reference position of a measurement range in the depth direction. The control is performed on the optical path length changing unit 114. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarization state of the reference light LR is adjusted for optimizing the interference efficiency between the measurement light LS and the reference light LR.

(Storage Unit 202)

The storage unit 202 stores various types of data. Examples of the data stored in the storage unit 202 include image data of an SLO image, image data of an OCT image, image data of a fundus image, image data of an anterior segment image, and subject's eye information. The subject's eye information includes information on the subject such as patient ID and name, and information on the subject's eye such as identification information of the left eye/right eye.

Further, the storage unit 202 stores correction data 202A. The correction data 202A is data for correcting the detection result of the interference light LC or the tomographic image formed based on the detection result in the depth direction (z direction), depending on a deflection angle of the measurement light LS deflected by the optical scanner 50 (at least one of the first galvano scanner and the second galvano scanner). In some embodiments, the correction data 202A is data for canceling an optical error in the optical system 10, depending on the deflection angle of the measurement light LS deflected by the optical scanner 50. In some embodiments, the correction data 202A is data for canceling the change in the optical path length caused by the displacement of the deflected surface of the optical scanner 50 with respect to the pupil conjugate position, depending on the deflection angle of the measurement light LS deflected by the optical scanner 50. In some embodiments, the correction data 202A is data for canceling an optical error in the optical system 10 and the change in the optical path length caused by the displacement of the deflected surface of the optical scanner 50 with respect to the pupil conjugate position, depending on the deflection angle of the measurement light LS deflected by the optical scanner 50

For example, the correction data 202A is generated by performing known ray trace processing on the optical system 10, corresponding to the deflection angle of the measurement light LS deflected by the optical scanner 50. For example, the correction data 202A is generated by analyzing the detection result of the interference light LC or the tomographic image formed based on the detection result. The detection result is acquired in correspondence with the deflection angle of the measurement light LS deflected by the optical scanner 50, by irradiating the object to be measured for calibration (for example, an object having a known shape such as a model eye) with the measurement light LS. Such generation of the correction data 202A is performed in a design process, in a shipping process, or during a plurality of OCT measurements.

In some embodiments, the storage unit 202 stores a plurality of correction data 202A corresponding to a plurality of scan modes of the measurement light LS.

In addition, the storage unit 202 stores various kinds of computer programs and data for operating the ophthalmologic apparatus 1.

(Image Forming Unit 210)

The image forming unit (image former) 210 include an SLO image forming unit 210A and an OCT image forming unit 210B. The SLO image forming unit 210A forms image data of the SLO image based on the detection signal input from the detector 26 and a pixel position signal input from the controller 200. The OCT image forming unit 210B forms an OCT image (image data) of the subject's eye E based on the sampling data obtained by sampling the detection signal from the detector 125 using the DAQ 130. The OCT image forming unit 210B forms image data of the OCT image based on the detection signal input from the DAQ 130 (detector 125) and a pixel position signal input from the controller 200. Examples of the OCT image formed by the OCT image forming unit 210B include an A-scan image, a B-scan image (tomographic image), a C-scan image, and the like. As with the conventional swept source OCT, the image formation process includes noise removal (noise reduction), filtering, dispersion compensation, fast Fourier transform (FFT), and the like. In the case of employing an OCT apparatus of another type, the image forming unit 210 performs known processing according to the type employed. The various images (the various image data) formed by the image forming unit 210 are stored in the storage unit 202, for example.

The functions of the image forming unit 210 are implemented by an image forming processor that realized the functions of the image forming unit 210.

(Data Processor 220)

The data processor 220 processes data acquired through SLO measurement for the subject's eye E or data acquired through OCT measurement for the subject's eye E. The data processor 220 performs various kinds of image processing and various kinds of analysis processing on the image formed by the image forming unit 210. For example, the data processor 220 performs various types of image correction such as brightness correction. In addition, the data processor 220 can also apply various kinds of image processing and various kinds of analysis processing to the image (e.g., the fundus image, the anterior segment image, or the like) obtained using the imaging optical system (not shown).

The data processor 220 performs known image processing such as interpolation for interpolating pixels in tomographic images to form three-dimensional image data of the fundus Ef. Note that image data of a three-dimensional image means image data in which the position of a pixel is defined by a three-dimensional coordinate system. Examples of the image data of the three-dimensional image include image data defined by voxels three-dimensionally arranged. Such image data is referred to as volume data or voxel data. When displaying an image based on volume data, the data processor 220 performs rendering (volume rendering, maximum intensity projection (MIP), etc.) on the volume data, thereby forming image data of a pseudo three-dimensional image viewed from a particular line of sight. This pseudo three-dimensional image is displayed on the display device included in the user interface unit 230.

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processor 220 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

The data processor 220 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 220 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 220 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 220 is also included in the OCT image.

Further, the data processor 220 determines the focus state of the measurement light LS in focus adjustment by analyzing the detection result of the interference light obtained by the OCT measurement. For example, the main controller 201 performs repetitive OCT measurements while controlling a focusing driver for driving the focusing lens according to a predetermined algorithm. The data processor 220 analyzes detection results of interference light LC repeatedly acquired by the OCT measurements to calculate predetermined evaluation values relating to image quality of OCT images. The data processor 220 determines whether the calculated evaluation value is equal to or less than a threshold. In some embodiments, the focus adjustment is continued until the calculated evaluation value becomes equal to or less than the threshold. That is, when the evaluation value is equal to or less than the threshold, it is determined that the focus state of the measurement light LS is appropriate. And the focus adjustment is continued until it is determined that the focus state of the measurement light LS is appropriate.

In some embodiments, the main controller 201 monitors the intensity of the interference signal (interference intensity, interference sensitivity) acquired sequentially while acquiring the interference signal by performing the repetitive OCT measurements described above. In addition, while performing this monitoring process, the focusing lens is moved to find the position of the focusing lens in which the interference intensity is maximized. With the focus adjustment thus performed, the focusing lens can be guided to the position where the interference intensity is optimized.

Further, the data processor 220 determines the polarization state of at least one of the measurement light LS and the reference light LR by analyzing the detection result of the interference light obtained by the OCT measurement. For example, the main controller 201 performs repetitive OCT measurements while controlling at least one of the polarization controllers 103 and 118 according to a predetermined algorithm. In some embodiments, the main controller 201 controls the attenuator 120 to change an attenuation of the reference light LR. The data processor 220 analyzes detection results of interference light LC repeatedly acquired by the OCT measurements to calculate predetermined evaluation values relating to image quality of OCT images. The data processor 220 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 201 can monitor the interference intensity also in the polarization adjustment.

Further, the data processor 220 performs predetermined analysis processing on the SLO image acquire by the SLO measurement, the detection result of the interference light acquired by the OCT measurement or the OCT image formed based on the detection result. Examples of the predetermined analysis processing include specifying (identification) of a predetermined site (tissue, lesion) of the subject's eye E; calculation of a distance between designated sites (distance between layers, interlayer distance), area, angle, ratio, or density; calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic papilla, a central fovea, a macula, and the like. Examples of the predetermined lesion include a leukoma, a hemorrhage, and the like.

(Correction Unit 221)

The data processor 220 includes a correction unit 221. The correction unit 221 corrects a position in the depth direction (z direction) of A-scan image (tomographic image) formed by the image forming unit 210 (OCT image forming unit 210B), based on the correction data 202A stored in the storage unit 202. In some embodiments, the correction unit 221 corrects the position in the depth direction of the detection result of the interference light LC sampled by the DAQ 130, based on the correction data 202A. Thereby, an optical error in the optical system 10 can be canceled, depending on the deflection angle of the measurement light LS deflected by the optical scanner 50. Further, the change in the optical path length caused by the displacement of the deflected surface of the optical scanner 50 with respect to the pupil conjugate position can be canceled, depending on the deflection angle of the measurement light LS deflected by the optical scanner 50.

Figure 5:
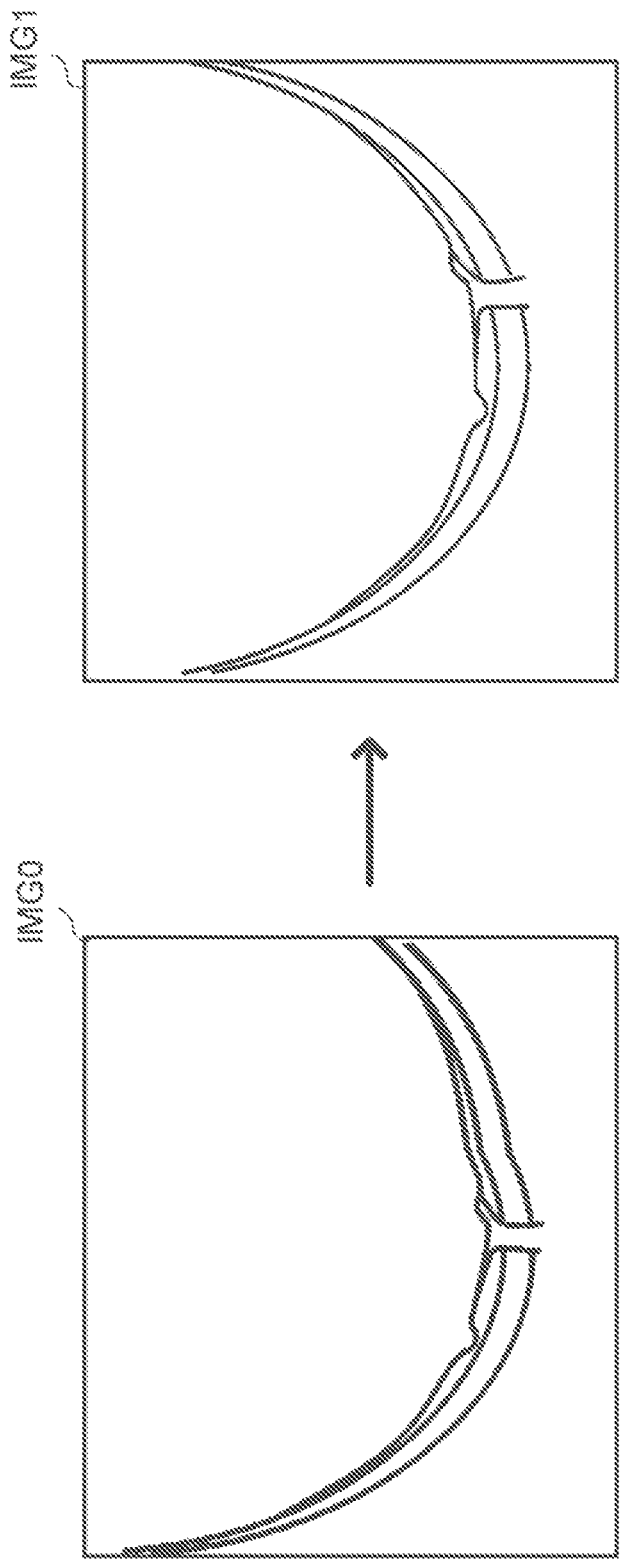
FIG. 5 is a schematic diagram for explaining processing performed by the ophthalmologic apparatus according to the embodiments.

FIG. 5 shows a diagram describing the operation of the ophthalmologic apparatus 1 according to the embodiments. FIG. 5 represents a diagram for explaining the change in the optical path length corresponding to the deflection angle of the optical scanner 50.

As described above, when the optical scanner 50 deflects the measurement light LS two-dimensionally, the deflected surface of the optical scanner 50 is displaced with respect to the pupil conjugate position. Thereby, in case of scanning the fundus Ef with the measurement light LS deflected by the optical scanner 50, the difference of the optical path length is changed depending on the deflection angle. In the A-scan image formed based on the detection result of the interference light LC in which the difference of the optical path length has changed, the depth position also changes as the difference of the optical path length changes. As a result, as shown in the tomographic image IMG0 in FIG. 5, an unnatural distortion in the depth direction depending on the deflection angle of the optical scanner 50 occurs.

On the other hand, as described above, the correction unit 221 can correct the A-scan image (or the detection result of the interference light LC) in the depth direction based on the correction data. Thereby, as shown in the tomographic image IMG1 in FIG. 5, a tomographic image without unnatural distortion similar to a tomographic image acquired by OCT measurement using another lens optical system can be acquired, without depending on the deflection angle of the optical scanner 50. Therefore, the measurement accuracy of OCT measurement acquired at a wider angle can be improved without reducing the measurement accuracy due to unnatural distortion.

The data processor 220 that functions as above includes, for example, a processor described above, a RAM, a ROM, a hard disk drive, a circuit board, and the like. In a storage device such as the hard disk drive, a computer program for causing the processor to execute the functions described above is stored in advance.

(User Interface Unit 230)

The user interface unit 230 has a function for exchanging information between a user and the ophthalmologic apparatus 1. The user interface unit 230 includes a display device and an operation device (an input device). The display device may include a display unit, and it may include another display device. The display device displays various information. The display device includes a liquid crystal display, for example. The display device displays the above information under the control of the main controller 201. Examples of the information displayed on the display device include information corresponding to the control result by the controller 200, information (image) corresponding to the calculation result by the image forming unit 210 or the data processor 220, and information (image) acquired by the optical system 10. The operation device includes various hardware keys and/or various software keys. Upon receiving the operation content for the operation device, the main controller 201 can output a control signal corresponding to the operation content to each part of the ophthalmologic apparatus. At least a part of the display device and at least a part of the operation device may be configured integrally. One example of this is the touch panel display.

The first ellipsoidal mirror 11A is an example of the "first concave mirror" according to the embodiments. The second ellipsoidal mirror 11B is an example the "second concave mirror" according to the embodiments. The optical system included in the SLO unit 20 is an example of the "SLO optical system" according to the embodiments. The optical system included in the OCT unit 100, the collimator lens unit 40, and the optical scanner 50 are an example of the "OCT optical system" according to the embodiments. The optical scanner 30A is an example of the "first optical scanner" according to the embodiments. The optical scanner 30B is an example of the "second optical scanner" according to the embodiments. The optical scanner 50 is an example of the "third optical scanner" according to the embodiments. The dichroic mirror DM is an example of the "optical path coupling member" according to the embodiments.

[Operation Example]

The operation of the ophthalmologic apparatus 1 according to the embodiments will be described.

Figure 6:
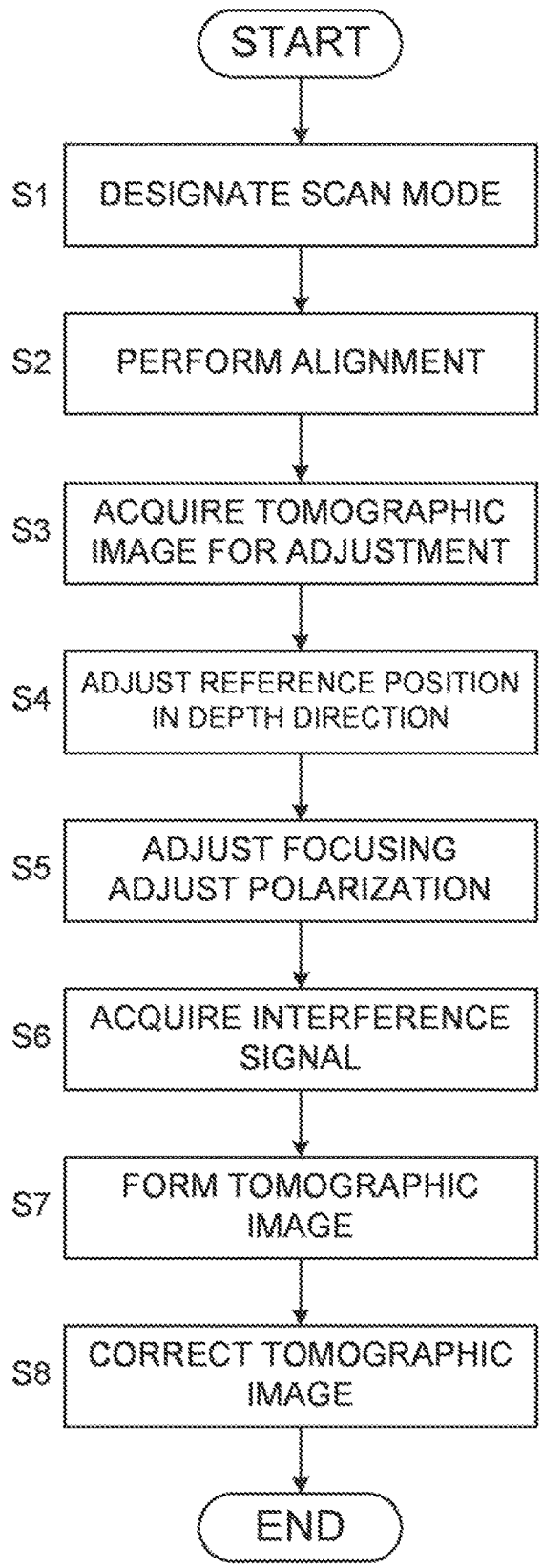
FIG. 6 is a flowchart illustrating an example of the operation of the ophthalmologic apparatus of the embodiments.

FIG. 6 shows an example of the operation of the ophthalmologic apparatus 1 according to the embodiments. FIG. 6 represents an example of the operation when OCT measurement is performed by the ophthalmologic apparatus 1. FIG. 6 shows a flowchart of the operation example of the ophthalmologic apparatus 1 according to the embodiments. The storage unit 202 stores computer programs for realizing the processing shown in FIG. 6. The main controller 201 operates according to the computer programs, and thereby the controller 200 (main controller 201) performs the processing shown in FIG. 6.

(S1: Designate Scan Mode)

The main controller 201 accepts designation of a scan mode from the user.

The user can designate the scan mode or the operation mode by operating the operation device in the user interface unit 230. When the scan mode (for example, horizontal scan, vertical scan) is designated by operating the operation device by the user, the main controller 201 analyzes an operation information from the operation device to specify the designated scan mode. When the operation mode is designated by operating the operation device by the user, the main controller 201 analyzes an operation information to specify a scan mode (for example, horizontal scan, vertical scan) designated in advance in the designated operation mode (for example, OCT measurement mode).

(S2: Perform Alignment)

Next, the main controller 201 performs alignment.

That is, the main controller 201 controls the alignment optical system (not shown) to project the alignment indicator onto the subject's eye E. At this time, a fixation target is also projected onto the subject's eye E. The main controller 201 controls the movement mechanism 10D based on the movement amount of the optical system to relatively move the optical system with respect to the subject's eye E by the movement amount. The movement amount is specified based on the receiving light image obtained using the SLO optical system or the imaging optical system (not shown), for example. The main controller 201 repeatedly executes this processing.

(S3: Acquire Tomographic Image for Adjustment)

The main controller 201 causes the fixation optical system (not shown) to project the fixation target for OCT measurement at a predetermined position, for example.

Subsequently, the main controller 201 controls the OCT unit 100 to perform OCT provisional measurement, and to acquire a tomographic image for adjustment for adjusting the reference position of the measurement range in the depth direction. Specifically, in a state where the optical scanner 30B is controlled to deflect the measurement light LS so as to irradiate a predetermined site (for example, the fundus Ef) of the fundus Ef, the main controller 201 controls the optical scanner 50 to deflect the measurement light LS generated based on the light L0 emitted from the OCT light source 101 and to scan the predetermined site of the subject's eye E with the deflected measurement light LS. The detection result of the interference light obtained by scanning with the measurement light LS is sent to the image forming unit 210 after being sampled in synchronization with the clock KC. The image forming unit 210 forms the tomographic image (OCT image) of the subject's eye E from the obtained interference signal.

(S4: Adjust Reference Position in Depth Direction)

Subsequently, the main controller 201 adjusts the reference position of the measurement range in the depth direction (z direction).

For example, the main controller 201 causes the data processor 220 to specify a predetermined site (for example, sclera) in the tomographic image obtained in step S3, and sets a position separated by a predetermined distance in the depth direction from the specified position of the predetermined site as the reference position of the measurement range. Alternatively, a predetermined position determined in advance so that the optical path lengths of the measurement light LS and the reference light LR substantially coincide may be set as the reference position of the measurement range.

(S5: Adjust Focusing, Adjust Polarization)

Next, the main controller 201 perform control of adjusting focusing and of adjusting polarization.

For example, the main controller 201 controls the OCT unit 100 to perform OCT measurement, after controlling the focusing driver (not shown) to move the focusing lens by a predetermined distance. The main controller 201 causes the data processor 220 to determine the focus state of the measurement light LS based on the detection result of the interference light acquired by the OCT measurement, as described above. When it is determined that the focus state is not appropriate based on the determination result of the data processor 220, the main controller 201 controls the focusing driver again and repeats this until it is determined that the focus state of the measurement light LS is appropriate.

Further, for example, the main controller 201 controls the OCT unit 100 to perform OCT measurement after controlling at least one of the polarization controllers 103 and 118 to change the polarization state of at least one of the light L0 and the measurement light LS by a predetermined amount. And then, the main controller 201 causes the image forming unit 210 to form the OCT image on the basis of the acquired detection result of the interference light. The main controller 201 causes the data processor 220 to determine the image quality of the OCT image acquired by the OCT measurement, as described above. When it is determined that the polarization state is not appropriate based on the determination result of the data processor 220, the main controller 201 controls the polarization controllers 103 and 118 again and repeats this until it is determined that the polarization state of the measurement light LS is appropriate.

(S6: Acquire Interference Signal)

Subsequently, the main controller 201 controls the optical scanner 30B to set the orientation of the deflected surface so as to irradiate a measurement range including a desired measurement site with the measurement light LS. With the orientation of the deflected surface of the optical scanner 30B fixed, the main controller 201 controls the optical scanner 50 to deflect the measurement light LS generated based on the light L0 emitted from the OCT light source 101 and to scan the predetermined site of the subject's eye E with the deflected measurement light LS. The detection result of the interference light acquired by the OCT measurement is sampled by the DAQ 130 and is stored as the interference signal in the storage unit 202 or the like.

(S7: Form Tomographic Image)

Next, the main controller 201 causes the image forming unit 210 to form a plurality of A-scan images of the fundus Ef along the B-scan direction, based on the interference signal acquired in step S6.

(S8: Correct Tomographic Image)

The main controller 201 causes the correction unit 221 to perform correction processing for adjusting the position in the depth direction depending on the deflection angle of the optical scanner 50 on at least a part of the plurality of A-scan images formed in step S7, based on the correction data 202A stored in the storage unit 202. Thereby, a new plurality of A-scan images can be acquired. The main controller 201 can cause the display device to display the B-scan image (tomographic image IMG1 in FIG. 5) based on the plurality of A-scan image generated newly.

This terminates the operation of the ophthalmologic apparatus 1 (END).

In the embodiments described above, the case where each of the optical scanners 30A, 30B, and 50 includes a galvano scanner has been described. However, the configuration according to the embodiments is not limited thereto. For example, at least one of the optical scanners 30A, 30B, and 50 may include a resonant mirror, a polygon mirror, or the like.

[Effects]

The ophthalmologic apparatus and the method of controlling the ophthalmologic apparatus according to the embodiments are explained.

An ophthalmologic apparatus (1) according to some embodiments includes a first concave mirror (first ellipsoidal mirror 11A), a second concave mirror (second ellipsoidal mirror 11B), an SLO optical system (optical system included in the SLO unit 20), a first optical scanner (optical scanner 30A), a second optical scanner (optical scanner 30B), an OCT optical system (optical system included in the OCT unit 100, the collimator lens unit 40, and the optical scanner 50), an optical path coupling member (dichroic mirror DM), and a correction unit (221). The first concave mirror has a concave surface-shaped first reflective surface. The second concave mirror has a concave surface-shaped second reflective surface. The SLO optical system is configured to project light from an SLO light source (21) onto a subject's eye (E) via the first concave mirror and the second concave mirror, and to detect returning light from the subject's eye. The first optical scanner is configured to deflect the light from the SLO light source to guide the light to the first reflective surface. The second optical scanner is configured to deflect light reflected by the first reflective surface to guide the light to the second reflective surface. The OCT optical system includes a third optical scanner (optical scanner 50), and is configured to split light (L0) from an OCT light source (101) into measurement light (LS) and reference light (LR), to project the measurement light deflected by the third optical scanner onto the subject's eye, and to detect interference light (LC) between returning light of the measurement light from the subject's eye and the reference light. The optical path coupling member is disposed between the first optical scanner and the first concave mirror, and combines an optical path of the SLO optical system and an optical path of the OCT optical system. The correction unit is configured to correct detection result of the interference light detected by the OCT optical system or an image (tomographic image, OCT image) formed based on the detection result.

According to such a configuration, an optical error including the first concave mirror, the second concave mirror, and the second optical scanner can be canceled corresponding to the deflection angle of the measurement light deflected by the third optical scanner. Thereby, an accurate measurement result can be obtained at a wider angle without being limited by tolerances of the optical system. Further, the change in the optical path length caused by the displacement of the deflected surface of the third optical scanner with respect to a pupil conjugate position can be canceled, depending on the deflection angle of the measurement light deflected by the third optical scanner. Thereby, an image without unnatural distortion similar to an image acquired by OCT measurement using another lens optical system can be acquired, without depending on the deflection angle of the third optical scanner. Therefore, measurement using a concave mirror can be performed at a wide angle at low cost and with high accuracy, without degrading measurement accuracy due to unnatural distortion.

The ophthalmologic apparatus according to some embodiments further includes a controller (200, main controller 201) configured: in a first operation mode (SLO measurement mode), to control the first optical scanner so as to one-dimensionally deflect the light from the SLO light source in a first direction (x direction); and to control the second optical scanner so as to one-dimensionally deflect the light deflected by the first optical scanner in a second direction (y direction) intersecting the first direction; and, in a second operation mode (OCT measurement mode), to control the third optical scanner so as to one-dimensionally deflect the measurement light in a third direction (x direction); and to control the second optical scanner so as to one-dimensionally deflect the measurement light deflected by the third optical scanner in a fourth direction (y direction) intersecting the third direction.

According to such a configuration, measurement accuracy of OCT measurement at a wider angle acquired can be improved while sharing the second optical scanner for SLO measurement and OCT measurement.

The ophthalmologic apparatus according to some embodiments further includes a controller (200, main controller 201) configured: in a first operation mode (SLO measurement mode), to control the first optical scanner so as to one-dimensionally deflect the light from the SLO light source in a first direction (x direction); and to control the second optical scanner so as to one-dimensionally deflect the light deflected by the first optical scanner in a second direction (y direction) intersecting the first direction; and, in a second operation mode (OCT measurement mode), to control the third optical scanner so as to two-dimensionally deflect the measurement light with deflection operation of the second optical scanner stopped.

According to such a configuration, a measurement at a wide angle using a concave mirror can be performed at low cost and with high accuracy.

In the ophthalmologic apparatus according to some embodiments, the controller is configured, in the second operation mode, to control the third optical scanner so as to two-dimensionally deflect the measurement light after controlling the second optical scanner so as to deflect the measurement light in a measurement direction corresponding to a measurement site of the subject's eye.

According to such a configuration, a measurement for a wide region including a measurement site of the subject's eye can be performed at low cost and with high accuracy using the concave mirror.

In the ophthalmologic apparatus according to some embodiments, the first reflective surface is an elliptical surface, the first optical scanner is disposed at a first focal point of the first concave mirror or near the first focal point, and the second optical scanner is disposed at a second focal point of the first concave mirror or near the second focal point.

According to such a configuration, a measurement at a wide angle using an ellipsoidal mirror can be performed at low cost and with high accuracy.

In the ophthalmologic apparatus according to some embodiments, the second reflective surface is an elliptical surface, the second optical scanner is disposed at a third focal point of the second concave mirror or near the third focal point, and the subject's eye is disposed at a fourth focal point of the second concave mirror or near the fourth focal point.

According to such a configuration, a measurement at a wide angle using an ellipsoidal mirror can be performed at low cost and with high accuracy.

The ophthalmologic apparatus according to some embodiments further includes a storage unit (202) configured to store correction data (202A) in advance. The correction unit is configured to correct a position of the detection result of the interference light or the image formed based on the detection result in a traveling direction (z direction, depth direction) of the measurement light, based on the correction data stored in the storage unit.

According to such a configuration, an image without unnatural distortion can be acquired with a simple configuration, without depending on the deflection angle of the third optical scanner. Therefore, measurement using a concave mirror can be performed at a wide angle at low cost and with high accuracy, without degrading measurement accuracy due to unnatural distortion.

In the ophthalmologic apparatus according to some embodiments, the correction data is data for correcting the detection result of the interference light or the image formed based on the detection result corresponding to a deflection angle of the measurement light deflected by the third optical scanner.

According to such a configuration, an image without unnatural distortion can be acquired, without depending on the deflection angle of the third optical scanner.

In the ophthalmologic apparatus according to some embodiments, the second optical scanner is configured to deflect the light from the SLO light source at a slower speed than the deflection speed of the first optical scanner.

According to such a configuration, known SLO measurement in which the first optical scanner deflects at high speed and the second optical scanner deflects at low speed can be performed.

A method of controlling an ophthalmologic apparatus according to some embodiments is a method of controlling an ophthalmologic apparatus (1) including: a first concave mirror (first ellipsoidal mirror 11A), a second concave mirror (second ellipsoidal mirror 11B), an SLO optical system (optical system included in the SLO unit 20), a first optical scanner (optical scanner 30A), a second optical scanner (optical scanner 30B), an OCT optical system (optical system included in the OCT unit 100, the collimator lens unit 40, and the optical scanner 50), and an optical path coupling member (dichroic mirror DM). The first concave mirror has a concave surface-shaped first reflective surface. The second concave mirror has a concave surface-shaped second reflective surface. The SLO optical system is configured to project light from an SLO light source (21) onto a subject's eye (E) via the first concave mirror and the second concave mirror, and to detect returning light from the subject's eye. The first optical scanner is configured to deflect the light from the SLO light source to guide the light to the first reflective surface. The second optical scanner is configured to deflect light reflected by the first reflective surface to guide the light to the second reflective surface. The OCT optical system includes a third optical scanner (optical scanner 50), and is configured to split light (L0) from an OCT light source (101) into measurement light (LS) and reference light (LR), to project the measurement light deflected by the third optical scanner onto the subject's eye, and to detect interference light (LC) between returning light of the measurement light from the subject's eye and the reference light. The optical path coupling member is disposed between the first optical scanner and the first concave mirror, and combines an optical path of the SLO optical system and an optical path of the OCT optical system. The method of controlling the ophthalmologic apparatus includes: an acquisition step of acquiring detection result of the interference light by performing optical coherence tomography on the subject's eye using the OCT optical system; and a correction step of correcting the detection result of the interference light acquired in the acquisition step or an image (tomographic image, OCT image) formed based on the detection result.

According to such a method, an optical error including the first concave mirror, the second concave mirror, and the second optical scanner can be canceled corresponding to the deflection angle of the measurement light deflected by the third optical scanner. Thereby, an accurate measurement result can be obtained at a wider angle without being limited by tolerances of the optical system. Further, the change in the optical path length caused by the displacement of the deflected surface of the third optical scanner with respect to a pupil conjugate position can be canceled, depending on the deflection angle of the measurement light deflected by the third optical scanner. Thereby, an image without unnatural distortion similar to an image acquired by OCT measurement using another lens optical system can be acquired, without depending on the deflection angle of the third optical scanner. Therefore, measurement using a concave mirror can be performed at a wide angle at low cost and with high accuracy, without degrading measurement accuracy due to unnatural distortion.

The method of controlling the ophthalmologic apparatus according to some embodiments further includes a first control step of, in a first operation mode (SL measurement mode), controlling the first optical scanner so as to one-dimensionally deflect the light from the SLO light source in a first direction (x direction); and of controlling the second optical scanner so as to one-dimensionally deflect the light deflected by the first optical scanner in a second direction (y direction) intersecting the first direction; and a second control step of, in a second operation mode (OCT measurement mode), controlling the third optical scanner so as to one-dimensionally deflect the measurement light in a third direction (x direction); and of controlling the second optical scanner so as to one-dimensionally deflect the measurement light deflected by the third optical scanner in a fourth direction (y direction) intersecting the third direction.

According to such a method, measurement accuracy of OCT measurement at a wider angle acquired can be improved while sharing the second optical scanner for SLO measurement and OCT measurement.

The method of controlling the ophthalmologic apparatus according to some embodiments further includes a first control step of, in a first operation mode (SLO measurement mode), controlling the first optical scanner so as to one-dimensionally deflect the light from the SLO light source in a first direction (x direction); and of controlling the second optical scanner so as to one-dimensionally deflect the light deflected by the first optical scanner in a second direction (y direction) intersecting the first direction; and a second control step of, in a second operation mode (OCT measurement mode), controlling the third optical scanner so as to two-dimensionally deflect the measurement light with deflection operation of the second optical scanner stopped.

According to such a method, a measurement at a wide angle using a concave mirror can be performed at low cost and with high accuracy.

In the method of controlling the ophthalmologic apparatus according to some embodiments, the second control step includes a step of controlling the third optical scanner so as to two-dimensionally deflect the measurement light after controlling the second optical scanner so as to deflect the measurement light in a measurement direction corresponding to a measurement site of the subject's eye.

According to such a method, a measurement for a wide region including a measurement site of the subject's eye can be performed at low cost and with high accuracy using the concave mirror.

In the method of controlling the ophthalmologic apparatus according to some embodiments, the first reflective surface is an elliptical surface, the first optical scanner is disposed at a first focal point of the first concave mirror or near the first focal point, and the second optical scanner is disposed at a second focal point of the first concave mirror or near the second focal point.

According to such a method, a measurement at a wide angle using an ellipsoidal mirror can be performed at low cost and with high accuracy.

In the method of controlling the ophthalmologic apparatus according to some embodiments, the second reflective surface is an elliptical surface, the second optical scanner is disposed at a third focal point of the second concave mirror or near the third focal point, and the subject's eye is disposed at a fourth focal point of the second concave mirror or near the fourth focal point.

According to such a method, a measurement at a wide angle using an ellipsoidal mirror can be performed at low cost and with high accuracy.

In the method of controlling the ophthalmologic apparatus according to some embodiments, the correction step includes a step of correcting a position of the detection result of the interference light or the image formed based on the detection result in a traveling direction (z direction, the depth direction) of the measurement light, based on correction data corresponding to a deflection angle of the measurement light deflected by the third optical scanner.

According to such a method, an image without unnatural distortion can be acquired with a simple configuration, without depending on the deflection angle of the third optical scanner. Therefore, measurement using a concave mirror can be performed at a wide angle at low cost and with high accuracy, without degrading measurement accuracy due to unnatural distortion.

<Others>

The above-described embodiments are merely examples for carrying out the present invention. Those who intend to implement the present invention can apply any modification, omission, addition, or the like within the scope of the gist of the present invention.

In some embodiments, a program for causing a computer to execute the method for controlling the ophthalmologic apparatus is provided. Such a program can be stored in any kind of recording medium that can be read by the computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus, comprising:
    a first concave mirror having a concave surface-shaped first reflective surface;
    a second concave mirror having a concave surface-shaped second reflective surface;
    a Scanning Laser Ophthalmoscope (SLO) optical system configured to project light from an SLO light source onto a subject's eye via the first concave mirror and the second concave mirror, and to detect returning light from the subject's eye;
    a first optical scanner configured to deflect the light from the SLO light source to guide the light to the first reflective surface;
    a second optical scanner configured to deflect light reflected by the first reflective surface to guide the light to the second reflective surface;
    an Optical Coherence Tomography (OCT) optical system including a third optical scanner, and configured to split light from an OCT light source into measurement light and reference light, to project the measurement light deflected by the third optical scanner onto the subject's eye, and to detect interference light between returning light of the measurement light from the subject's eye and the reference light, the third optical scanner being disposed at a pupil conjugate position optically substantially conjugate with a pupil of the subject's eye or near the pupil conjugate position;
    an optical path coupling member disposed between the first optical scanner and the first concave mirror, and combining an optical path of the SLO optical system and an optical path of the OCT optical system; and
    a correction unit configured to correct detection result of the interference light detected by the OCT optical system or an image formed based on the detection result, the correction unit being configured to correct a position of the detection result of the interference light or the image formed based on the detection result, along a traveling direction of the measurement light, so as to cancel a change in an optical path length caused by a displacement of a deflected surface of the third optical scanner with respect to the pupil conjugate position depending on a deflection angle of the measurement light by the third optical scanner.

2. The ophthalmologic apparatus of claim 1, further comprising
    a controller configured:
    in a first operation mode,
    to control the first optical scanner so as to one-dimensionally deflect the light from the SLO light source in a first direction; and
    to control the second optical scanner so as to one-dimensionally deflect the light deflected by the first optical scanner in a second direction intersecting the first direction; and,
    in a second operation mode,
    to control the third optical scanner so as to one-dimensionally deflect the measurement light in a third direction; and
    to control the second optical scanner so as to one-dimensionally deflect the measurement light deflected by the third optical scanner in a fourth direction intersecting the third direction.

3. The ophthalmologic apparatus of claim 1, further comprising
    a controller configured:
    in a first operation mode,
    to control the first optical scanner so as to one-dimensionally deflect the light from the SLO light source in a first direction; and
    to control the second optical scanner so as to one-dimensionally deflect the light deflected by the first optical scanner in a second direction intersecting the first direction; and,
    in a second operation mode,
    to control the third optical scanner so as to two-dimensionally deflect the measurement light with deflection operation of the second optical scanner stopped.

4. The ophthalmologic apparatus of claim 3, wherein
    the controller is configured:
    in the second operation mode,
    to control the third optical scanner so as to two-dimensionally deflect the measurement light after controlling the second optical scanner so as to deflect the measurement light in a measurement direction corresponding to a measurement site of the subject's eye.

5. The ophthalmologic apparatus of claim 1, wherein
    the first reflective surface is an elliptical surface,
    the first optical scanner is disposed at a first focal point of the first concave mirror or near the first focal point, and
    the second optical scanner is disposed at a second focal point of the first concave mirror or near the second focal point.

6. The ophthalmologic apparatus of claim 1, wherein
    the second reflective surface is an elliptical surface,
    the second optical scanner is disposed at a third focal point of the second concave mirror or near the third focal point, and the subject's eye is disposed at a fourth focal point of the second concave mirror or near the fourth focal point.

7. The ophthalmologic apparatus of claim 1, further comprising
a storage unit configured to store correction data in advance, wherein
the correction unit is configured to correct a position of the detection result of the interference light or the image formed based on the detection result in a traveling direction of the measurement light, based on the correction data stored in the storage unit.

8. The ophthalmologic apparatus of claim 7, wherein
the correction data is data for correcting the detection result of the interference light or the image formed based on the detection result corresponding to a deflection angle of the measurement light deflected by the third optical scanner.

9. The ophthalmologic apparatus of claim 1, wherein
the second optical scanner is configured to deflect the light from the SLO light source at a slower speed than the deflection speed of the first optical scanner.

10. A method of controlling an ophthalmologic apparatus including:
a first concave mirror having a concave surface-shaped first reflective surface;
a second concave mirror having a concave surface-shaped second reflective surface;
a Scanning Laser Ophthalmoscope (SLO) optical system configured to project light from an SLO light source onto a subject's eye via the first concave mirror and the second concave mirror, and to detect returning light from the subject's eye;
a first optical scanner configured to deflect the light from the SLO light source to guide the light to the first reflective surface;
a second optical scanner configured to deflect light reflected by the first reflective surface to guide the light to the second reflective surface;
an Optical Coherence Tomography (OCT) optical system including a third optical scanner, and configured to split light from an OCT light source into measurement light and reference light, to project the measurement light deflected by the third optical scanner onto a subject's eye, and to detect interference light between returning light of the measurement light from the subject's eye and the reference light, the third optical scanner being disposed at a pupil conjugate position optically substantially conjugate with a pupil of the subject's eye or near the pupil conjugate position; and
an optical path coupling member disposed between the first optical scanner and the first concave mirror, and combining an optical path of the SLO optical system and an optical path of the OCT optical system, the method comprising:
an acquisition step of acquiring detection result of the interference light by performing optical coherence tomography on the subject's eye using the OCT optical system; and
a correction step of correcting the detection result of the interference light acquired in the acquisition step or an image formed based on the detection result, the correction step including correcting a position of the detection result of the interference light or the image formed based on the detection result, along a traveling direction of the measurement light, so as to cancel a change in an optical path length caused by a displacement of a deflected surface of the third optical scanner with respect to the pupil conjugate position depending on a deflection angle of the measurement light by the third optical scanner.

11. The method of controlling the ophthalmologic apparatus of claim 10, further including
a first control step of, in a first operation mode,
controlling the first optical scanner so as to one-dimensionally deflect the light from the SLO light source in a first direction; and of controlling the second optical scanner so as to one-dimensionally deflect the light deflected by the first optical scanner in a second direction intersecting the first direction; and
a second control step of, in a second operation mode,
controlling the third optical scanner so as to one-dimensionally deflect the measurement light in a third direction; and of controlling the second optical scanner so as to one-dimensionally deflect the measurement light deflected by the third optical scanner in a fourth direction intersecting the third direction.

12. The method of controlling the ophthalmologic apparatus of claim 10, further including
a first control step of, in a first operation mode,
controlling the first optical scanner so as to one-dimensionally deflect the light from the SLO light source in a first direction; and of controlling the second optical scanner so as to one-dimensionally deflect the light deflected by the first optical scanner in a second direction intersecting the first direction; and
a second control step of, in a second operation mode,
controlling the third optical scanner so as to two-dimensionally deflect the measurement light with deflection operation of the second optical scanner stopped.

13. The method of controlling the ophthalmologic apparatus of claim 12, wherein
the second control step includes a step of controlling the third optical scanner so as to two-dimensionally deflect the measurement light after controlling the second optical scanner so as to deflect the measurement light in a measurement direction corresponding to a measurement site of the subject's eye.

14. The method of controlling the ophthalmologic apparatus of claim 10, wherein
the first reflective surface is an elliptical surface,
the first optical scanner is disposed at a first focal point of the first concave mirror or near the first focal point, and
the second optical scanner is disposed at a second focal point of the first concave mirror or near the second focal point.

15. The method of controlling the ophthalmologic apparatus of claim 10, wherein
the second reflective surface is an elliptical surface,
the second optical scanner is disposed at a third focal point of the second concave mirror or near the third focal point, and
the subject's eye is disposed at a fourth focal point of the second concave mirror or near the fourth focal point.

16. The method of controlling the ophthalmologic apparatus of claim 10, wherein
the correction step includes a step of correcting a position of the detection result of the interference light or the image formed based on the detection result in a traveling direction of the measurement light, based on correction data corresponding to a deflection angle of the measurement light deflected by the third optical scanner.

* * * * *